United States Patent [19]

Adair

[11] Patent Number: 5,188,094
[45] Date of Patent: Feb. 23, 1993

[54] HEAT STERILIZABLE ELECTRONIC VIDEO ENDOSCOPE

[76] Inventor: Edwin L. Adair, 2800 S. University Blvd., Denver, Colo. 80210

[21] Appl. No.: 769,120

[22] Filed: Sep. 30, 1991

[51] Int. Cl.⁵ ............................................. A61B 1/06
[52] U.S. Cl. ................................... 128/6; 128/4; 359/512; 359/820
[58] Field of Search ................ 358/98; 128/6, 4; 359/512, 820

[56] References Cited

U.S. PATENT DOCUMENTS

| | | | |
|---|---|---|---|
| 3,261,349 | 7/1966 | Wallace | 128/6 |
| 3,321,265 | 5/1967 | Clave et al. | 359/512 X |
| 3,592,199 | 7/1971 | Ostensen | |
| 4,319,563 | 3/1982 | Kubota | 128/6 |
| 4,590,923 | 5/1986 | Watanabe | |
| 4,646,723 | 3/1987 | Arakawa | |
| 4,745,471 | 5/1988 | Takamura et al. | |
| 4,762,120 | 8/1988 | Hussein | |
| 4,822,154 | 4/1989 | Oxford et al. | 128/6 X |
| 4,832,003 | 5/1989 | Yabe | |
| 4,850,674 | 7/1989 | Hasselskog | 359/820 |
| 4,854,302 | 8/1989 | Allred, III | |
| 4,867,137 | 9/1989 | Takahashi | |
| 4,878,485 | 11/1989 | Adair | |
| 4,896,941 | 1/1990 | Hayashi et al. | 128/6 |
| 4,914,521 | 4/1990 | Adair | |
| 4,921,326 | 5/1990 | Wild et al. | 128/6 X |
| 4,966,439 | 10/1990 | Althaus et al. | 359/820 |
| 4,971,035 | 11/1990 | Ito | |
| 4,993,405 | 2/1991 | Takamura et al. | 128/6 |

Primary Examiner—Richard J. Apley
Assistant Examiner—Karen A. Jalbert
Attorney, Agent, or Firm—Fields, Lewis, Pittenger & Rost

[57] ABSTRACT

A heat sterilizable electronic video endoscope is provided in which a lens system is mounted by the use of elements such as metal spacers, which are not adversely affected by heat. Similarly, the electronic circuitry is arranged in the center of the endoscope and is formed of heat resistant material. In addition, glass fibers are provided which surround the lens system and the electronic circuitry to further protect it from the heat of sterilization. The light fibers themselves are made of glass and are not adversely affected by the heat sterilizing process. In addition, a sterilizable sheath may be provided which will extend over the endoscope and has an accordion shaped extension to extend along the electrical cable and light cable for those situations where it is not possible to resterilize the endoscope for a second procedure. In addition, a removable handle can be provided over the sheath which facilitates positioning the endoscope during an operative procedure or investigation.

6 Claims, 3 Drawing Sheets

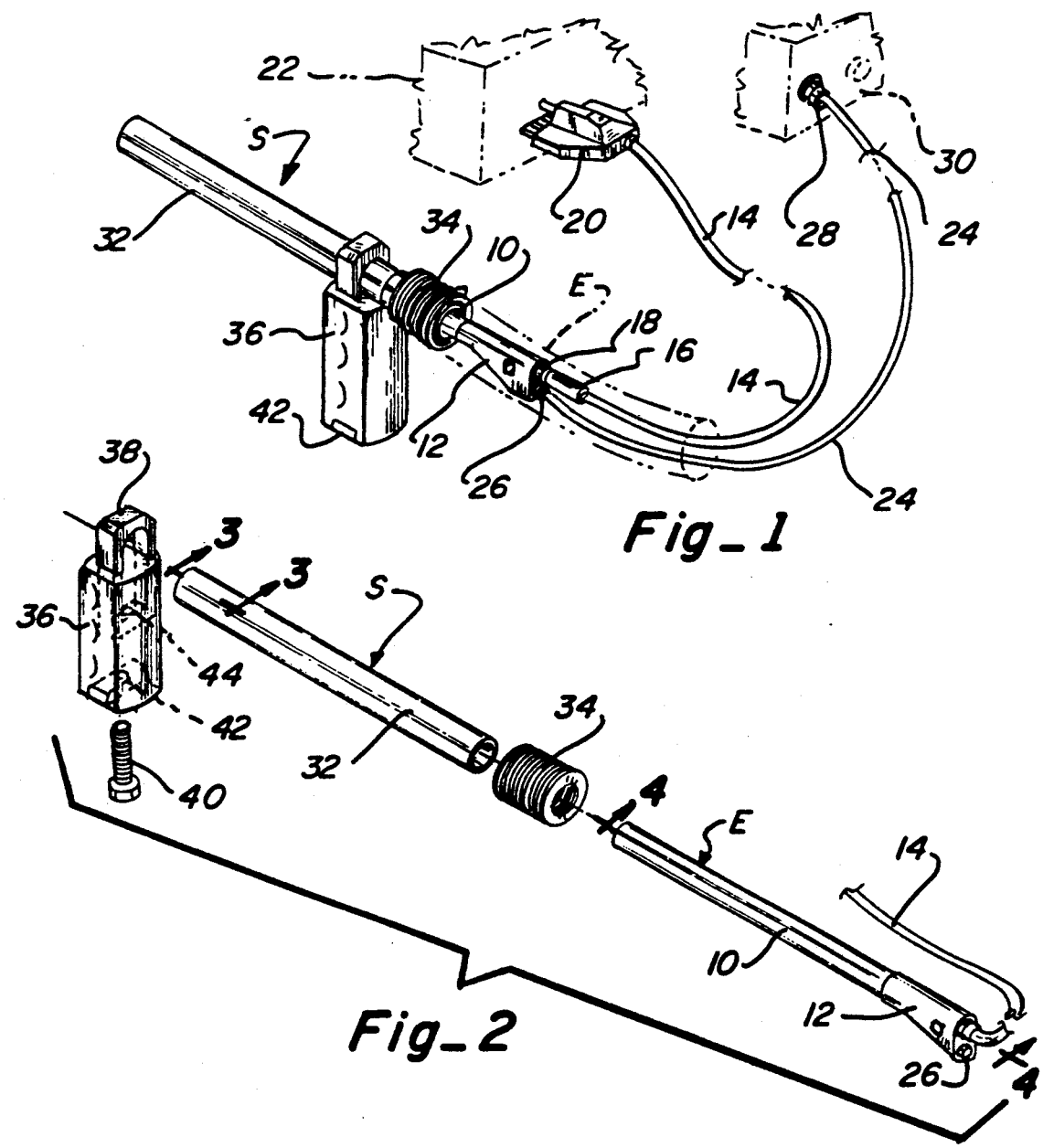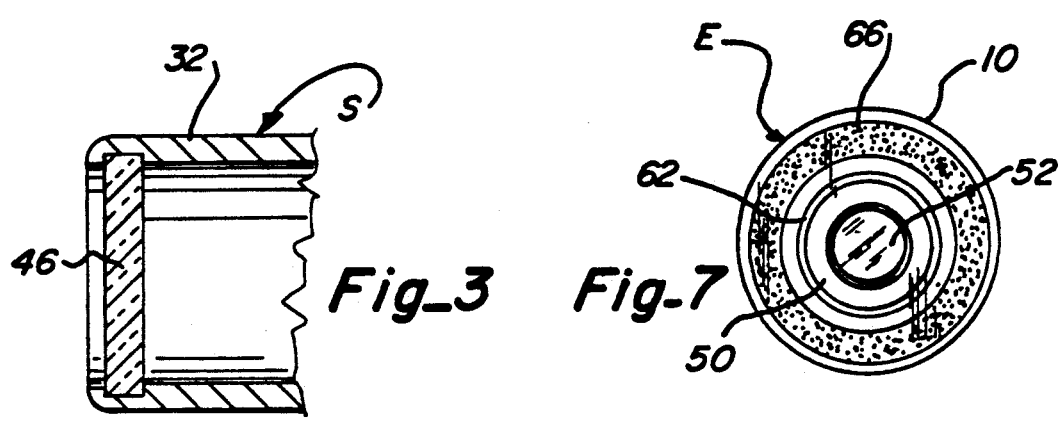

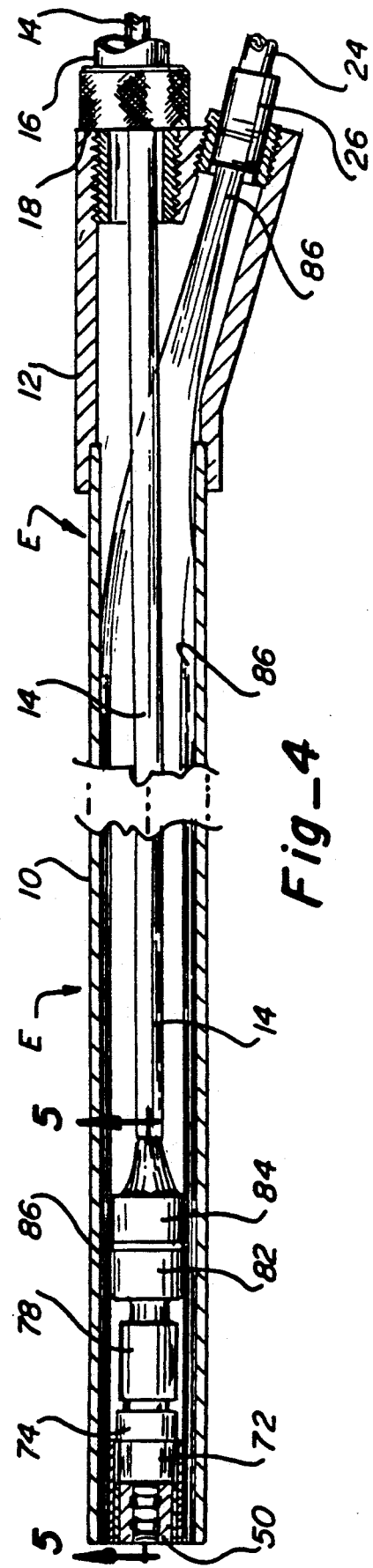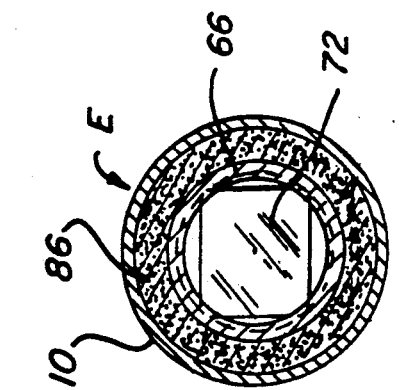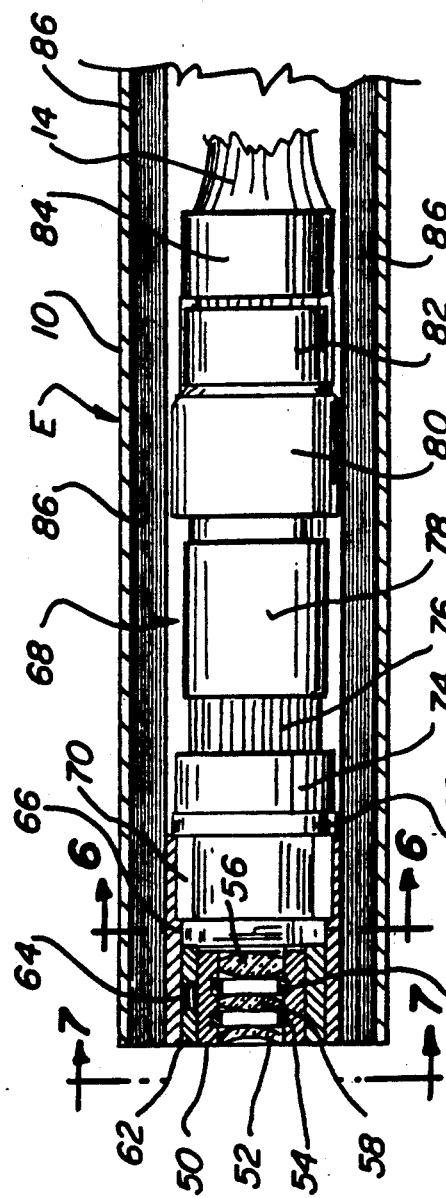

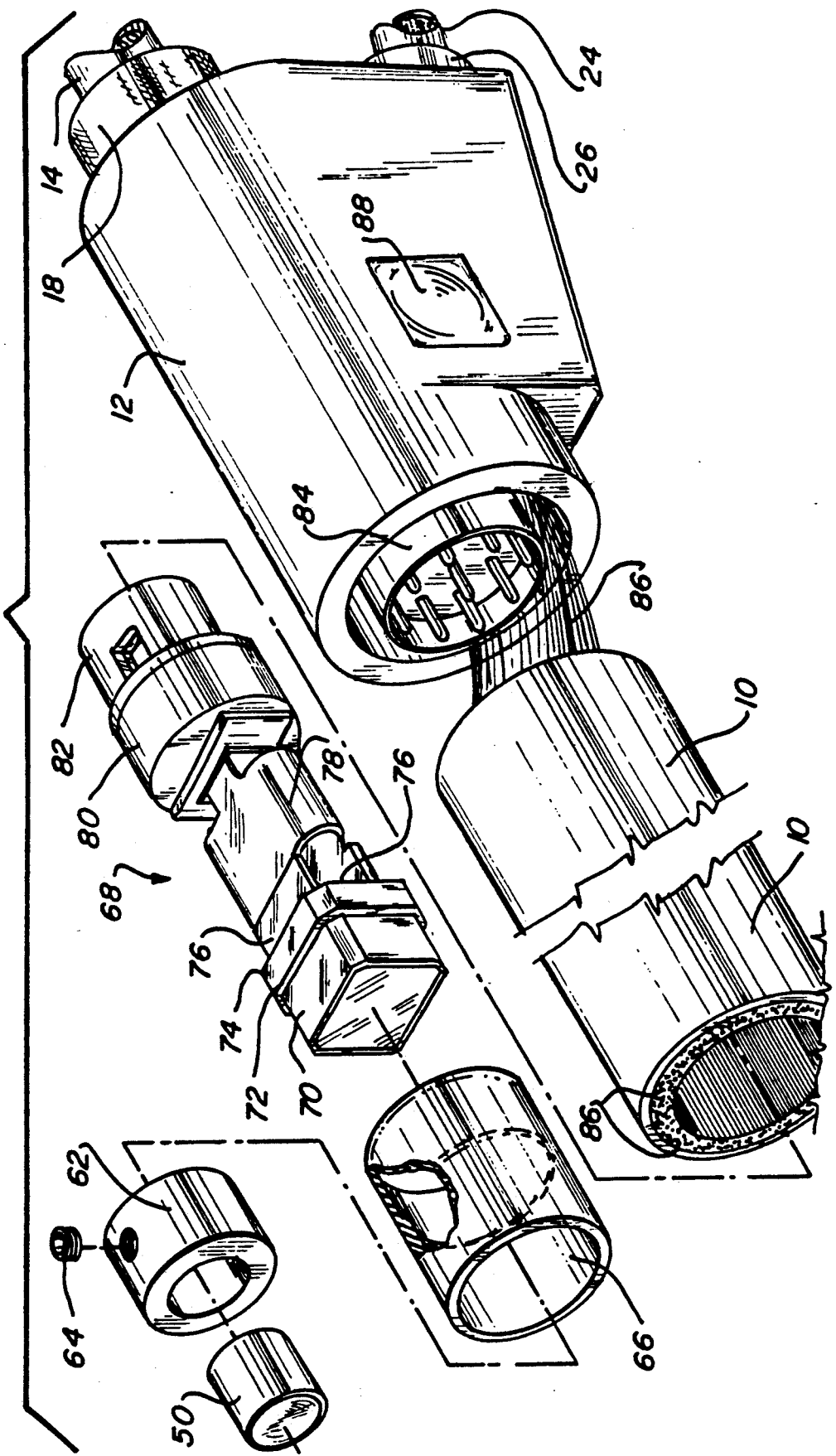

HEAT STERILIZABLE ELECTRONIC VIDEO ENDOSCOPE

TECHNICAL FIELD

This invention relates to a sterilizable electronic video endoscope and more particularly to one which is sterilizable by heat thereby reducing the sterilizing time required.

BACKGROUND ART

Endoscopes are very expensive instruments which normally are not disposable. Therefore, they must be sterilized between uses on different patients to minimize the possibility of infection and the transmittal of disease. Currently, the only method of sterilizing is by soaking the endoscope in a disinfecting solution such as Cidex. While this solution renders the device essentially sterile, there is still some danger of transmitting disease utilizing soaking solutions.

Endoscopes as presently constructed, cannot be sterilized with heat because the heat causes the adhesive between the compound lenses in the endoscope to come apart. This is particularly true after repeated exposure to high temperatures. Of course, when these lenses fall apart the endoscope is useless and must be repaired or replaced.

Sterilizable or disposable sheaths have been provided on endoscopes which cannot be heat sterilizable as shown in my U.S. Pat. No. 4,878,485 and on cameras which cannot be heat sterilizable, as shown in my U.S. Pat. No. 4,914,521.

U.S. Pat. No. 3,592,199 to Ostensen discloses an autoclavable power pack unit for an endoscope in which a combination light source and power pack is autoclavable, including the lens. A tubular portion is mounted on a handle by a pair of clamping screws.

U.S. Pat. No. 4,590,923 to Watanabe discloses an arthroscope-video camera assembly that has a video camera enclosed in a stainless steel housing. The housing may be autoclavable for multiple procedures.

U.S. Pat. No. 4,646,723 to Arakawa et al. discloses an endoscope having a lens system. A heat conductive material is provided to permit heat accumulated in the lens system to be emitted to the outside.

U.S Pat. No. 4,745,471 to Takamura et al. discloses an endoscope in which lenses are separated from one another by an unspecified annular element and mounted in front of a solid-state chip.

U.S. Pat. No. 4,762,120 to Hussein discloses an endoscope with a handle that is threadably received in the body of the endoscope.

U.S. Pat. No. 4,832,003 to Yabe discloses an electronic endoscope tip having a spacer provided in the lens system.

U.S. Pat. No. 4,854,302 to Allred, III discloses a video equipped endoscope with a needle probe that has a CCD solid-state imager and a probe which is sterilizable, as by soaking. The probe includes a lens, a main rod, seal and fiber optic bundle.

U.S. Pat. No. 4,867,137 to Takahashi discloses an endoscope with lenses separated from one another by an unspecified annular element. The device uses a solid-state image sensor.

U.S. Pat. No. 4,971,035 to Ito discloses an endoscope having a CCD image sensor. A spacer is provided in the lens arrangement between the lenses.

While all of the foregoing devices are satisfactory for their intended purpose, none of them provide a heat sterilizable endoscope as suggested by the present invention.

DISCLOSURE OF THE INVENTION

In accordance with this invention, a heat sterilizable electronic video endoscope is provided which has a tubular housing with a distal end and a proximate end. A plurality of lenses are provided which form an objective lens system. A lens conversion tube having a diameter less than that of the tubular housing and metal spacers support the lenses in spaced position within the tube at the distal end of the tubular housing for receiving a light image. A CCD is mounted in the tubular housing at the image plane of the objective lens system for sensing an image. Circuitry is connected to the CCD upstream thereof and provided with a connector. A CCD electrical cable is provided in a heat resistant sheath having a connector releasably connected to the circuitry connector and extending axially along the tubular housing to the distal end thereof. Light transmitting glass fibers completely surround the lens conversion tube, the CCD, the circuitry and the CCD electric cable.

The endoscope also includes a hollow hand grip having a first end attached to the proximate end of the tubular housing and a first opening at the second end through which the electrical cable extends and a second opening through which the glass fibers extend. A light source connector is secured to the glass fibers in the second opening.

The device can also include an outer CCD alignment tube, an inner CCD alignment tube concentrically mounted within the outer CCD alignment tube, the lens conversion tube being mounted in the distal end of the inner CCD alignment tube and the CCD being mounted in the proximate end of the outer CCD alignment tube. An I.R. filter can be mounted in the proximate end of the outer CCD alignment tube in juxtaposition to the proximate end of the inner CCD alignment tube.

An elongated sterile sheath, having a closed distal end and an open proximate end, is extendable over the tubular housing and the hollow hand grip. An expandable sleeve is attached to the proximate end of the sheath and extendable over the electrical cable and the light transmitting cable. A removable handle can be connected to the sheath, the handle having a bracket extending around the sheath and means for tightening and loosening the bracket.

The advantage of the foregoing described invention is that an endoscope is provided which is heat sterilizable so that it can be quickly made sterile for reuse on one patient after another. For even more rapid reuse, a sterilizable sheath can be placed over the endoscope and replaced after each use.

Additional advantages of this invention will become apparent, from the description as follows, taken in conjunction with the accompanying drawings.

BRIEF DESCRIPTION OF THE DRAWINGS

FIG. 1 is a perspective view of a heat sterilizable endoscope constructed in accordance with this invention;

FIG. 2 is an exploded view of the heat sterilizable endoscope of FIG. 1;

FIG. 3 is an enlarged fragmentary horizontal section, taken along line 3—3 of FIG. 2, showing the distal end of the sheath;

FIG. 4 is a fragmentary enlarged longitudinal section, taken along line 4—4 of FIG. 2, showing internal details of the heat sterilizable endoscope;

FIG. 5 is an enlarged section, taken along line 5—5 of FIG. 4, showing details of the lens mounting, CCD and electronics for the heat sterilizable endoscope;

FIG. 6 is a vertical section, taken along line 6—6 of FIG. 5, showing the mounting for the CCD;

FIG. 7 is an end view of the endoscope, taken along line 7—7 of FIG. 5; and

FIG. 8 is an exploded view showing further details of the lens mounting, the CCD and associated circuitry.

BEST MODE FOR CARRYING OUT THE INVENTION

In accordance with this invention, a sterilizable electronic video endoscope is provided, as shown in FIG. 1, having a tubular housing 10 with a proximate end connected to a hollow hand grip 12. The proximate end of hand grip 12 has two outlets, a first outlet is for receiving an electrical cable 14 whose distal end extends through a strain relief member 16 and into a connector 18. The other end of electrical cable 14 is fastened to a terminal 20 which is connectable to a VCR 22. A light cable 24 has a distal end connected to a connector 26 in hand grip 10. The opposite end of light cable 24 is connected to an interface member 28 attachable to a suitable light source 30.

Optionally, a sterilizable sheath S of the type shown in my U.S. Pat. No. 4,878,485 for "Rigid Video Endoscope With Heat Sterilizable Sheath" can be provided. The subject matter of that patent is incorporated herein by reference. The sheath S has a cylindrical body 32 which is receivable over tubular housing 10 and includes an accordion shaped sleeve 34 which is connected to the proximate end thereof and is extendable, as shown in dotted lines in FIG. 1, over the distal ends of electrical cable 14 and light cable 24.

Conveniently, a handle 36 is removably received over body 32 and has a U-shaped yoke 38 which can be clamped down against the body by tightening a threaded member, such as screw 40 which extends through a bracket 42 at the lower end of the handle and is threadably received in an opening 44 at the lower end of yoke 38. This handle can be sterilized with heat.

The purpose of the sterilizable sheath is to provide the physician and the hospital with two options. The endoscope can be resterilized after each use which takes about fifteen minutes, or the sheath can be replaced with another sterilizable sheath so that another operation can be performed immediately.

The distal end of body 32 of sheath S has a transparent window 46, as shown in FIG. 3, through which light may be projected from and images received into the end of endoscope E, as will be more clearly apparent from the description below.

The details of the endoscope E can best be seen by referring to FIGS. 4–8. A cylindrical lens housing 50 houses a lens system centrally within housing 10 and comprises multiple lenses, such as lenses 52, 54 and 56 which are separated and held in place by metal spacers 58 and 60, respectively, as shown. The number of lenses and spacers can be varied depending upon the size and use for which the endoscope is designed. However, it is important to note that the metal spacers hold the lenses in proper orientation with respect to each other without the use of adhesives or other materials that are deleteriously affected by heat. Plus, the lens system can be sterilized with heat without coming apart or otherwise degrading. Lens housing 50 is held in place within a collar 62 by means of a set screw 64. This collar in turn is mounted within the distal end of sleeve 66 which is substantially longer than collar 62.

The electronic circuitry 68, as best seen in FIG. 5 and 8, includes, in series, an I.R filter 70, a CCD 72, a terminal board 74, terminal array 76, a folded circuit board 78 and a connector 80 having a female receptacle 82 which receives male plug 84 on electrical cable 14.

Advantageously, glass fibers 86 are packed densely circumferentially all the way around the centrally mounted lens system and electronic circuitry thus described and are gathered together within housing 12 and terminate at connector 26. Light cable 24 attaches to connector 28 and supplies light from light source 30. Light for illumination is provided through glass fibers 86 and is reflected from the site under investigation through the lens system to the CCD where the images are converted into electrical signals to be supplied through electrical cable 14 to VCR 22. Of course, the VCR can be connected to a TV monitor (not shown) so that in addition to recording the event, the physician can look at the monitor to view the site under investigative or operative procedures.

A control 88 can be provided on the side of housing 12 for controlling the VCR. In particular, a pause button is desirable so that recording is only done at the times which the physician considers appropriate.

From the foregoing, the advantages of this invention are readily apparent. A relatively simple and compact endoscope is provided which is heat sterilizable so that it can be quickly reused on a second patient after use on a first patient. In addition, where resterilization may not be practical or necessary, a sterilizable sheath can be provided over the endoscope which has a removable handle to help control the positioning of the endoscope during the operative or investigative procedure.

This invention has been described in detail with reference to a particular embodiment thereof, but it will be understood that various other modifications can be effected within the spirit and scope of this invention.

What is claimed is:

1. A heat sterilizable electronic video endoscope comprising:
    an endoscope tubular housing having a distal end and a proximate end;
    a plurality of lenses, forming an objective lens system;
    a lens conversion tube having a diameter less than that of said tubular housing and heat resistant metal spacers solely supporting said lenses in spaced position and centrally locating said lenses within said tube at said distal end of said tubular housing when receiving a light image during use and during heat sterilization;
    a CCD centrally mounted in said tubular housing at the image plane of said objective lens system for sensing an image;
    circuitry connected to said CCD upstream thereof and provided with a connector;
    a CCD electrical cable in a heat resistant sheath having a connector releasably connected to said circuitry connector and extending axially along said tubular housing and through said distal end thereof; and light transmitting glass fibers completely surrounding said lens conversion tube, said CCD, said circuitry and said CCD electric cable, protecting all of them from the heat of sterilization.

2. Apparatus, as claimed in claim 1, further including:
a generally hollow hand grip having a first end attached to said proximate end of said tubular housing and a first opening through which said electrical cable extends and a second opening through which said glass fibers extend; and
a light source connector secured to said glass fibers in said second opening.

3. Apparatus, as claimed in claim 2, further including:
an elongated sterile sheath, having a closed distal end and an open proximate end, extendable over said tubular housing and said hollow hand grip; and
an expandable sleeve attached to said proximate end of said sheath and extendable over said electrical cable and a light transmitting cable.

4. Apparatus, as claimed in claim 3, further including:
a removable handle connectable to said sheath, said handle having:
a bracket extendable around said sheath; and
means for tightening and loosening said bracket.

5. Apparatus, as claimed in claim 1, further including:
an outer CCD alignment tube;
an inner CCD alignment tube concentrically mounted within said outer CCD alignment tube, said lens conversion tube being mounted in the distal end of said inner CCD alignment tube and said CCD being mounted on the proximate end of said outer CCD alignment tube in the image plane of said lens system.

6. Apparatus, as claimed in claim 5, further including:
an I.R. filter mounted in said proximate end of said outer CCD alignment tube in juxtaposition to the proximate end of said inner CCD alignment tube.

* * * * *